United States Patent [19]

Iqbal

[11] 3,968,159

[45] July 6, 1976

[54] PROCESS FOR PREPARING AZOMETHINES

[75] Inventor: Abul F. M. Iqbal, Glattbrugg, Switzerland

[73] Assignee: Monsanto Company, St. Louis, Mo.

[22] Filed: May 23, 1974

[21] Appl. No.: 472,763

Related U.S. Application Data

[63] Continuation-in-part of Ser. No. 282,620, Aug. 21, 1972, abandoned.

[30] Foreign Application Priority Data

Aug. 31, 1971 Switzerland.................. 12751/71

[52] U.S. Cl............................................ 260/566 F
[51] Int. Cl.$^2$........................................ C07C 119/10
[58] Field of Search....... 260/566 R, 240 G, 583 M, 260/566 N, 566 F, 566 D

[56] References Cited
UNITED STATES PATENTS 2,388,903  11/1945  Cantrell et al.............. 260/240 G
3,293,295  11/1966  Swakon et al................ 260/580
3,637,820   1/1972  Dodman et al................ 260/580

FOREIGN PATENTS OR APPLICATIONS 441,179    1/1925  Germany

OTHER PUBLICATIONS

Wagner et al., Synthetic Organic Chemistry Chapman and Hall, Lmtd., N.Y., N.Y. 1953 p. 728–729.

*Primary Examiner*—Arthur P. Demers

[57] ABSTRACT

Azomethines are prepared by reacting under carbon monoxide pressure an aromatic or heterocyclic aldehyde and an aromatic or heterocyclic nitro compound in the presence of a tertiary amine and Group VIII metal carbonyl. Exemplary is the preparation of benzylidene-aniline by reaction of benzaldehyde and nitrobenzene in the presence of pyridine and $Rh_6(CO)_{16}$ at 170°C and 150 atmospheres.

5 Claims, No Drawings

PROCESS FOR PREPARING AZOMETHINES

This application is a continuation-in-part of Ser. No. 282,620, filed Aug. 21, 1972, now abandoned.

BACKGROUND OF THE INVENTION

1. Field of the Invention

This invention relates to a process for the preparation of aromatic or heterocyclic azomethines. In a more particular aspect, this invention relates to a process for the preparation of said azomethines by reaction of an aromatic or heterocyclic aldehyde and an aromatic or heterocyclic nitro compound under carbon monoxide pressure.

2. Description of the Prior Art

Numerous azomethines, also known as Schiff bases, aldehyde imines and aldimines, are known to the art. The preparation of azomethines is known to the art and various processes for their preparation are described in the book of Saul Patai "The Chemistry of the Carbon Nitrogen Double Bond" (Interscience Publishers — 1970). One well known procedure for preparing azomethines comprises reacting an aldehyde and a primary amine. Other procedures known to the art involve the reaction of an aldehyde with (1) an isocyanate

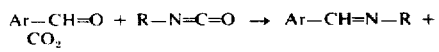

or with (2) a sulfurdiimide

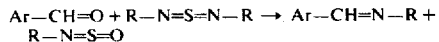

or with (3) a carbodiimide

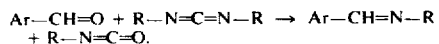

The aldehyde-amine reaction is generally preferred to the other three reactions in the preparation of azomethines principally due to the high cost of the isocyanate, sulfurdiimide and carbodiimide starting materials, but also due to instability of these compounds which make them more difficult to handle than the amines.

SUMMARY OF THE INVENTION

It has been discovered in accordance with the present invention that aromatic or heterocyclic azomethines are obtained by reacting a corresponding aldehyde with a corresponding nitro compound under carbon monoxide pressure in a solvent which is a basic tertiary amine or amide and in the presence of catalytic amounts of a Group VIII metal carbonyl compound. The process of the present invention is preferred to the aldehyde-amine process of the prior art since it does not require the prior reduction of the nitro compound to the corresponding amine. Thus, the process of the present invention affords the art a one-step process for the preparation of azomethines wherein the starting material is an aromatic or heterocyclic nitro compound.

DETAILED DESCRIPTION

In carrying out the process of the present invention an aromatic or heterocyclic aldehyde and an aromatic or heterocyclic nitro compound are reacted under carbon monoxide pressure in a basic solvent which is a tertiary amine or amide in the presence of a metal carbonyl compound as catalyst, the metal being selected from the Group VIII metals of the Periodic Table. The reaction occurs according to the equation

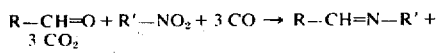

wherein R and R' represent aromatic or heterocyclic radicals which may have substituents such as halo,

wherein R'' is lower alkyl (1–8 carbon atoms), alkoxy (1–8 carbon atoms) and phenoxy. An advantage of the process of the present invention is that neither amines, hydroxylamines or isocyanates are formed. While not being bound by any particular theory, it is believed that the formation of the azomethine proceeds through an intermediate compound which is a nitrene according to the scheme

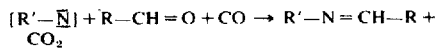

In the process of the present invention any suitable aromatic or heterocyclic aldehyde can be employed with large numbers of such aldehydes being known and available. Such suitable aldehydes include benzaldehyde, diphenylaldehyde, terphenylaldehyde, naphthaldehyde, anthraldehyde, benzanthraldehyde and other polynuclear aldehydes. Moreover, pyridinecarboxaldehyde, morpholinecarboxaldehyde etc. Such suitable alehydes may, if desired, contain inert substituents such as halogen atoms, alkyl, alkoxy, alkylenedioxy, phenoxy, ester and t-amino groups. Examples of such substituted aldehydes include chlorobenzaldehyde, trichlorobenzaldehyde, tetrachlorobenzaldehyde and pentachlorobenzaldehyde, as well as the corresponding iodo, bromo and fluoro compounds. Additional examples of such substituted alehydes include tolualdehyde, mesityaldehyde, anisaldehyde, ethoxybenzaldehyde, veratraldehyde, protocatechaldehyde, cumaldehyde, piperonal, phenoxybenzaldehyde, dimethylaminobenzaldehyde, acetoxybenzaldehyde, carbomethoxybenzaldehyde, carbophenoxybenzaldehyde, vanillin acetate and the like.

In the process of the present invention any suitable aromatic or heterocyclic nitro compound can be employed with large numbers of such nitro compounds being known and available. Examples of such nitro compounds include nitrobenzene, the nitrodiphenyls, nitronaphthalenes and nitropyridines. The nitro compounds can, if desired, be substituted in the manner of the aldehydes.

The solvents employed in the process of the present invention are basic tertiary amines and basic tertiary amides. Examples of suitable basic tertiary amines include triethylamine, N,N-dimethylbutylamine, pyridine, dimethylaminopyridine, N-methylpyrrolidine, N-ethylpiperidine, N,N'-dimethylpiperazine, pentamethylguanidine etc. and the like.

The basic tertiary amines are generally preferred to the amides as the solvents for the process of the present invention with strongly basic amines i.e. those having a dissociation constant in aqueous solution of at least pKa=10 being especially preferred. The tertiary amines play an important role in the reduction, while not being limited to a particular theory, it is believed that the amine plays a role in the formation of and enhances the stability of the catalytic species which is believed to be hydrido-carbonylmetal derivatives. Also the amine serves to capture the carbon dioxide formed in the reaction. Basic tertiary amides are also useful as solvents in the process of the present invention. The simple tertiary amides permit but do not, as is the case with the suitable amines, promote the reaction. The weekly basic dimethylformamide and the more strongly basic tetramethylurea are more effective than the simple tertiary amides.

The advantage in the use of a basic tertiary amine is apparent when benzene is used as the only solvent and from about 5 to 7% azomethine is formed whereas when pyridine is employed as the only solvent under the same conditions 80% and more azomethine is obtained. The present invention includes the use of solvent mixtures comprising an inert solvent and a basic tertiary amine or amide. In all cases, the solvent medium employed should be liquid at reaction temperatures. The amount of solvent employed will typically be an excess amount, e.g. 6 moles or more per nitro group.

The catalyst employed in the process of the present invention comprises carbonyl compounds of metals of Group VIII of the Periodic Table. Such catalysts are known and are commonly used in catalytic carbonylation reactions. The valency of the originally engaged metal salt or compound is not significant because the metal carbonyl compounds acting as catalysts will generally be formed under the reaction conditions. Thus, the catalyst may be formed "in situ" or can be prepared in a separate step. Methods for the preparation of such catalysts are well-known to the art. The preferred catalysts for use in the process of the present invention are the rhodium compounds for example, the rhodium carbonyls such as $Rh_4(CO)_{12}$ and $Rh_6(CO)_{16}$ and the rhodium oxides such as $RhO_2$ and $Rh_2O_3$, the rhodium oxides being appropriate for the preparation of catalysts in situ.

The process of the present invention is carried out under carbon monoxide pressure under reaction conditions. The pressure (CO) can vary over a wide range with pressures in the range of from about 50 to about 500 atmospheres being typically employed. The reaction temperature may also vary over a wide range with temepratures in the range of from about 50° to about 250°C being typically employed. When temperatures lower than 50°C and pressures lower than 50 atm. are employed it is particularly desirable to use a strong tertiary base as the solvent.

Aromatic azomethines are known to the art and there uses are described in the technical literature. For example, they are useful as antioxidants for polyester oils (U.S. Pat. No. 3,201,350), phenols (British Pat. No. 787,859), paraffinic turbine oils (British Pat. No. 738,093) and for lubricants (German Pat. No. 942,523). Also they are useful as accelerating agents for curing elastic diisocyanate-modified polyesters (British Pat. No. 712,053) as drying accelerators in paints (German Pat. No. 974,727), as disinfectants, e.g. bactericides (Chemical Abstracts 44, 1440 h) and fungicides (Chemical Abstracts 48, 10838 e and 49, 13593 C) as catalysts in the reaction of polyisocyanates with polyhydroxy compounds (German Pat. No. 1,033,896), in coatings of electrophotographic papers (British Pat. No. 836,151), for the stabilization of jet fuels (U.S. Pat. No. 3,034,876, and for color correction masks in the cyanide layer of color films (German Pat. No. 950,617).

The following examples illustrate specific embodiments of the invention.

TABLE I

PREPARATION OF AZOMETHINE

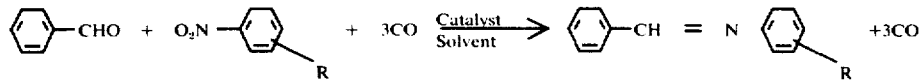

| Example Number | Nitro derivative (R=) | Yield of Azomethine (based on benzaldehyde) | Remarks |
|---|---|---|---|
| 1 | H | 80 | Traces of carbanilide formed as byproduct |
| 2 | H" | 6 | |
| 3 | m-Cl | 25–30 | Appreciable formation (ca.50%)of 3.3'-dichloroazobenzene |
| 4 | p-OCH₃ | 60 | As byproduct could be identified traces of N.N'di-(p-methoxyphenyl)-urea and p-anisidine. Considerable formation of a tarry residue entailed difficulty in recrystallizing the Azomethine base. |
| 5 | p-N(CH₃)₂ | 60–70 | Similar manifestations as in the case of p-nitroanisole above. |
| 6 | o-CH₃ | 82 | Traces of N.N'di(o-tolyl)-urea formed as byproduct. |
| 7 | m-CH₃ | 85 | Traces of N-N'-di(m-tolyl)-urea formed as byproduct. |
| 8 | p-CH₃ | 83 | In contrast to o- and m-nitrotoluenes, considerable formation of a non-volatile residue, beside p-toluidine and traces of urea. |
| 9 | p-C₆H₅ | 84 | |

"in 50 ml benzene instead of pyridine as solvent.

| Boiling point or melting point (uncorrected) | IR (C=N)ᵇ [μ] | H¹—NMR Chemical Shift | | [ppm]ᶜ |
|---|---|---|---|---|
| | | –CH=N– | aromatic | –CH₃ |
| 88–92°C/0.3 torr | 6.15 | 8.28 | 6.9–8.0 | — |
| 71–72°C | 6.15 | 8.3 | 6.65–7.95 | 3.7 |
| 98–99°C | 6.19 | 8.37 | 6.5–7.95 | 2.93 |
| 94–98°C/0.4 torr | 6.12 | 8.17 | 6.6–7.95 | 2.32 |

TABLE I-continued

| | | | | |
|---|---|---|---|---|
| 90–93°C/0.3 torr | 6.15 | 8.25 | 6.7–7.95 | 2.31 |
| 97–100°C/0.3 torr | 6.14 | 8.24 | 6.8–7.9 | 2.26 |
| 147°C | 6.16 | 8.41 | 7.05–8.05 | — |

<sup>a</sup>Liquids were measured neat, solids in chloroform.
<sup>b</sup>NMR spectra were taken in carbon tetrachloride.

EXAMPLES 1–9

Azomethines were prepared using the following general procedure:

Benzaldehyde (0.1 mole), aromatic nitro compound (0.11 mole), hexarhodium hexadecacarbonyl ($5 \times 10^{-5}$ mole) and dry pyridine (50 ml) are charged to a 0.5 liter stainless steel rocking autoclave. The autoclave is pressurized with carbon monoxide to 150 atmospheres the contents are heated to 170°C, and the reaction is allowed to proceed for 3 hours. On completion of the 3 hour reaction period, the autoclave contents are cooled, reaction gases are vented and the mixture is discharged. The reaction mixture is distilled directly with the corresponding azomethine being obtained either by fraction of the distillate or by fractionation crystallization of the solvent-free residue. The results are given in Table 1. Identity of the azomethine compounds was confirmed by IR and NMR spectroscopic comparison with known samples.

EXAMPLE 10

A solution of β-naphthaldehyde (0.1 mole), nitrobenzene (0.11 mole) and rhodium hydroxide [Rh(OH)$_3$] in 50 ml of pyridine were charged into a stainless steel rocking autoclave of 0.5 l capacity. The autoclave was pressurized to 140 atm with carbon monoxide and heated to 170°C for 3 hours. On completion of the reaction period, the pressure vessel was allowed to cool and the gases vented. Work-up of the reaction mixture gave 75% yield of β-naphthylideneaniline, the product being unequivocally identified by mixed melting point and spectroscopic (ir and nmr) comparison with an authentic sample.

EXAMPLE 11

By a procedure essentially similar to that of Example 10, however employing as catalyst Rh$_4$(CO)$_{12}$ in place of Rh(OH)$_3$, p-(N.N-dimethylamino)benzaldehyde and nitrobenzene were converted in about 60% yield to the corresponding Schiff base, namely p-(N.N-dimethylamino)benzylideneaniline.

EXAMPLE 12 m-Tolualdehyde and [Rh(OCOCH$_3$)$_2$]$_2$ were substituted for the respective reactant and catalyst of Example 10. The yield of toluylideneaniline was about 80%.

EXAMPLE 13 p-Chlorobenzaldehyde and [Rh(CO)$_2$Cl]$_2$ were substituted for the respective reactant and catalyst of Example 10. The yield of p-chlorobenzylideneaniline was 85%.

EXAMPLE 14

Anisaldehyde and tris-triphenylphosphine-rhodium-chloride were substituted for the respective reactant and catalyst of Example 10. The yield of anisylideneaniline was about 50%.

EXAMPLE 15

A solution of benzaldehyde (0.1 mole) and 3-nitropyridine (0.11 mole) in 50 ml of pyridine was reacted in the presence of Rh$_6$(CO)$_{16}$ as in Example 10. The yield of benzylidene-3-aminopyridine was about 50%. The product was identified by elemental micro analysis and spectroscopic (ir, nmr) comparison with an authentic sample.

EXAMPLE 16

1-Nitronaphthalene and RhCl$_3$.3H$_2$O were substituted for the respective reactant and catalyst of Example 15. The yield of benzylidene-3-aminonaphthalene was about 85%. The product was identified by mixed melting point and spectroscopic (ir, nmr) comparison with an authentic sample.

EXAMPLE 17

5-Nitroquinoline was substituted for 3-nitropyridine of Example 15. The yield of benzylidene-5-aminoquinoline was 74%.

EXAMPLE 18 p-Nitrobenzoic acid methylester was substituted for 3-nitropyridine of Example 15. The yield of benzylidene-4-aminobenzoic acid methylester was about 60%.

While the invention has been described with reference to particular embodiments thereof, it will be appreciated that modifications and variations are possible without departing from the invention.

I claim:

1. A process for the preparation of aromatic or heterocyclic azomethines which consists essentially of reacting under carbon monoxide pressure of 50 to about 500 atmospheres and a temperature of 50°–250°C, an aromatic or heterocyclic aldehyde, and an aromatic or heterocyclic nitro compound in the presence of a solvent containing a compound selected from the group consisting of basic tertiary amines and basic tertiary amides, and of a catalyst selected from the group consisting of [Rh(CO)$_2$Cl]$_2$, [Rh(O-COCH$_3$)$_2$]$_2$, Rh$_4$(CO)$_{12}$, Rh$_6$(CO)$_{16}$, RhCl[(C$_6$H$_5$)$_3$P]$_3$, RhO$_2$, Rh$_2$O$_3$, Rh(OH)$_3$ and RhCl$_3$ the molar ratio of said catalyst relative to the said nitro compound being from 1:100 to 1:50,000.

2. The process of claim 1 wherein the catalyst is selected from the group consisting of Rh$_6$(CO)$_{16}$ and Rh$_4$(CO)$_{12}$.

3. The process of claim 1 wherein the solvent is pyridine.

4. The process of claim 1 wherein the solvent is a tertiary amine having a dissociation constant in aqueous solution of at least pKa = 10.

5. A process for the preparation of aromatic azomethines which comprises reacting under carbon monoxide pressure of 50 to about 500 atmospheres, and a temperature of 50°–250°C, benzaldehyde and a nitrobenzene in the presence of pyridine as a solvent, and of hexarhodium hexadecacarbonyl as a catalyst, which catalyst is present in the molar ratio relative to the said nitrobenzene of 1:100 to about 1:50,000.

* * * * *